(12) United States Patent
Faulkner et al.

(10) Patent No.: US 6,740,041 B2
(45) Date of Patent: May 25, 2004

(54) BONE DENSITOMETER PROVIDING ASSESSMENT OF ABSOLUTE FRACTURE RISK

(75) Inventors: Kenneth G. Faulkner, Verona, WI (US); Howard Stavers Barden, Madison, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/065,137

(22) Filed: Sep. 19, 2002

(65) Prior Publication Data

US 2004/0059223 A1 Mar. 25, 2004

(51) Int. Cl.⁷ .................................. A61B 8/02
(52) U.S. Cl. ....................................... 600/449
(58) Field of Search ................. 600/407–471; 378/54, 56, 62, 51, 174, 196, 208, 98.2, 98.3, 98.9, 146; 73/620–633; 367/7, 11, 130, 138; 128/898, 916

(56) References Cited

U.S. PATENT DOCUMENTS

| | | | | |
|---|---|---|---|---|
| 4,829,549 A | * | 5/1989 | Vogel et al. | 378/55 |
| 5,291,537 A | * | 3/1994 | Mazess | 378/54 |
| 5,509,042 A | * | 4/1996 | Mazess | 378/54 |
| 5,840,029 A | * | 11/1998 | Mazess et al. | 600/437 |
| 6,027,449 A | * | 2/2000 | Mazess et al. | 600/449 |
| 6,160,866 A | * | 12/2000 | Mazess et al. | 378/56 |
| 6,215,846 B1 | * | 4/2001 | Mazess et al. | 378/62 |
| 6,246,745 B1 | * | 6/2001 | Bi et al. | 378/54 |
| 6,320,931 B1 | * | 11/2001 | Arnold | 378/56 |
| 6,385,283 B1 | * | 5/2002 | Stein et al. | 378/54 |

* cited by examiner

Primary Examiner—Ali M. Iman
(74) Attorney, Agent, or Firm—Quarles & Brady LLP; Carl Holton

(57) ABSTRACT

A bone densitometer accepts inputs of non-bone density patient information to provide a measure of absolute fracture risk to provide a more accurate and personal assessment of osteoporosis. A simple graphical output compares this risk to standard populations.

21 Claims, 2 Drawing Sheets

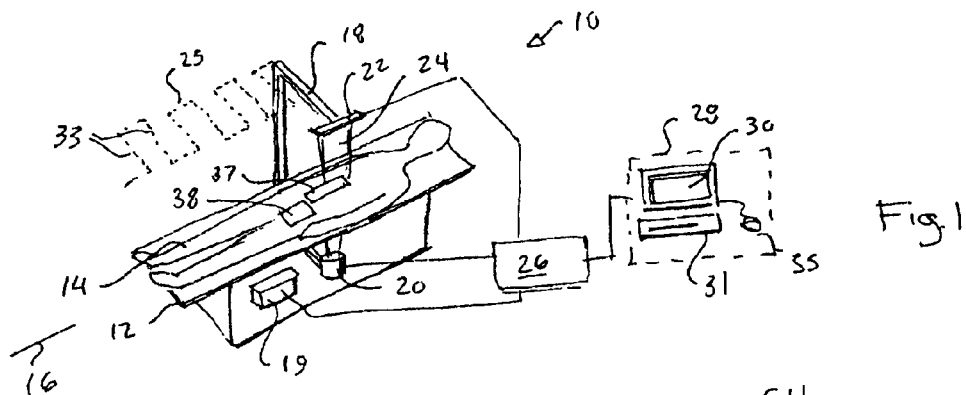
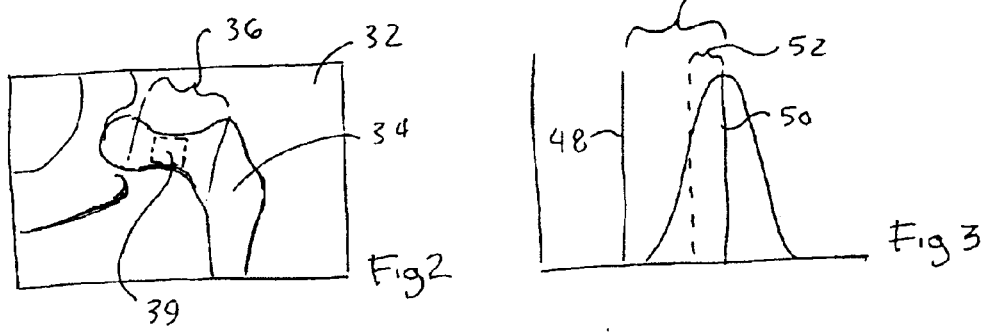
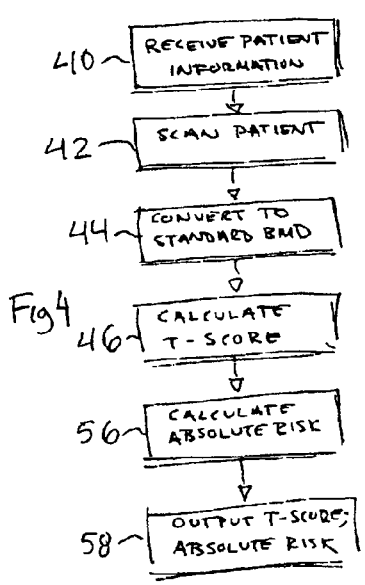
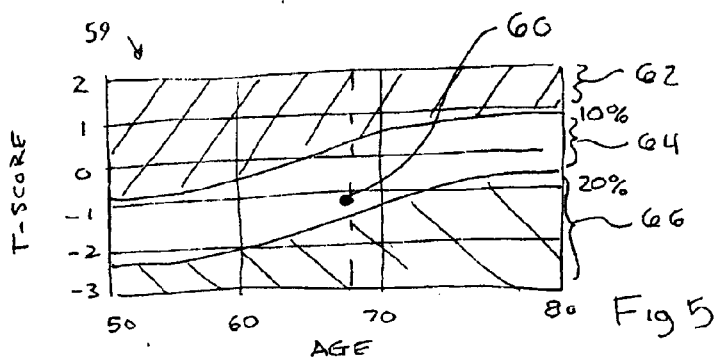

US 6,740,041 B2

BONE DENSITOMETER PROVIDING ASSESSMENT OF ABSOLUTE FRACTURE RISK

BACKGROUND OF INVENTION

The present invention relates to diagnostic medical equipment and in particular to a bone densitometer providing an output indicating absolute risk of bone fracture.

Bone densitometers provide a measurement of bone mineral density (BMD) typically using x-ray or ultrasound measurement. Normally this BMD value is an areal density measurement, e.g., $g/cm^2$, however, volume density measurements, e.g. $g/cm^3$, may also be provided using, for example, tomographic reconstruction.

BMD measurements may be made at various locations on the body but are most frequently conducted on the bones of the lumbar vertebra, the femoral neck, or the os calcis of the heel.

X-ray and ultrasound densitometers are described in U.S. Pat. Nos. 6,438,201, 6,364,837, 6,277,076, 6,246,747, 6,215,846, 6,160,866, 6,081,582, 6,038,281, 6,027,449, RE361 62, 5,841,833, 5,840,029, and 5,748,704, among others, assigned to the assignee of the present invention and hereby incorporated by reference.

A raw BMD value has limited meaning to a physician or patient and so current densitometers normally provide a comparison of the measured BMD value to an established reference. One such reference is a T-score, which compares the patient's BMD value to the expected value of BMD for a young adult of the same gender. The T-score provides a qualitative indication of risk of fracture in that the greater the negative value of the T-score, the greater the risk of fracture.

Alternatively, a logistic regression analysis may be used to determine a quantitative relationship between BMD and relative fracture risk based on a recognized mathematical relationship between decline in BMD and increased risk of fracture. This relationship has been determined prospectively in empirical studies of elderly populations and considers the difference between the patient and someone of the same age and gender.

Desirably, bone densitometry equipment would provide an indication of the patient's absolute fracture risk. In this respect, T-scores and relative risk measurements are inadequate. For example, a 70 year old patient with a T-score of −2 and relative risk of 4 has much greater absolute fracture risk than a 50 year old patient with the same T-score and relative risk.

SUMMARY OF INVENTION

The present inventors have recognized that measurement of BMD produced by densitometry equipment, cannot alone provide an indication of absolute fracture risk. To the contrary, current studies show that absolute fracture risk is strongly dependent on factors that are independent of BMD, in particular, age and gender. Other factors which affect absolute fracture risk include: whether the patient is a smoker, the amount of exercise the patient gets, how much the patient is on his/her feet, the patient's history of fractures, the patient's family history of fractures, and the long axis length of the patient's hip (hip axis length). It is likely that additional risk factors will be discovered.

The present invention therefore provides a bone densitometer that accepts additional patient data to produce an output measurement of absolute fracture risk. The physician and patient are presented with this absolute fracture risk contemporaneously with the measurement of BMD, reducing patient confusion about T-scores and relative risk, and eliminating the need for cumbersome additional calculations by the physician.

BRIEF DESCRIPTION OF DRAWINGS

FIG. 1 is a simplified perspective view of an x-ray bone densitometer providing for lateral scanning or anterior/posterior scanning of a patient with an x-ray fan beam under the control of a computer;

FIG. 2 is a bone image of the femur such as may be acquired from the apparatus of FIG. 1 showing measurement of patient hip axis length and placement of a region of interest on the neck of the femur;

FIG. 3 is a graph plotting as vertical bars average bone density in the region of interest of FIG. 2, average bone density of a standard individual for the same region of interest, and standard deviation of measurement of the standard individual used in the calculation of T-score;

FIG. 4 is a flow chart showing steps performed by a program executed by the computer of FIG. 1 to provide an output measure of absolute fracture risk;

FIG. 5 shows an example of a graphic output of absolute fracture risk;

FIG. 6 is an example of a tabular output of absolute fracture risk;

DETAILED DESCRIPTION

Figure 7:
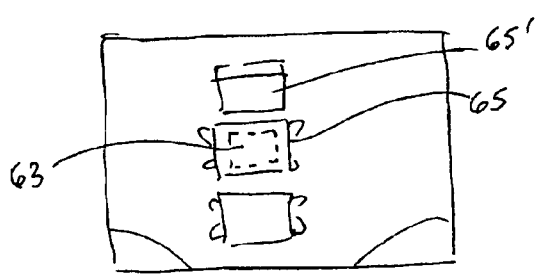
FIG. 7 is a figure similar to that of FIG. 2 showing use of the invention on lumbar vertebrae and a positioning of a region of interest upon one vertebra.

Referring now to FIG. 1, an x-ray bone densitometer 10 may include a patient table 12 providing a horizontal surface for supporting a patient in supine position along the longitudinal axis 16.

A C-arm 18 may have a lower end positioned beneath the patient table 12 to support an x-ray source 20 and, an upper end positioned above the patient table to support an opposed x-ray detector 22. The x-ray source 20 produces a fan beam 24 whose plane is parallel to the longitudinal axis 16, and which, in the preferred embodiment, provides two x-ray energies. The x-ray detector 22 may be a multi-element CZT detector discriminating between the energies of x-rays. Other methods of dual energy measurement, including those providing for rotating filter wheels or variations in x-ray tube voltage, may also be used, as may monoenergetic techniques of measuring bone density, as will be understood in the art.

The x-ray source 20 and x-ray detector 22 may be moved in a raster pattern 25 so as to trace a series of transverse scans 33 of the patient during which dual energy x-ray data is collected by the x-ray detector 22. The raster pattern 25 is adjusted so that there is a slight overlap between successive scan lines of the fan beam 24 to provide some height data. During this scanning, the x-ray source 20, the x-ray detector 22, and the translation controller 19 communicate with and are under the control of computer 26 which may include dedicated circuitry and/or one or more processors. The operation of the computer 26 is under the direction of a stored program portion of which will be described in detail below.

The computer 26 communicates with a terminal 28 including a display 30 and a keyboard 31 and a cursor control device such as a mouse 35 allowing for operator input of patient data, as will be described, and the output of text and/or images to the operator providing the results of the scan.

During operation of the bone densitometer 10 to acquire bone mineral density (BMD) data, the computer 26 will communicate with the translation controller 19 to scan a region of interest (37 or 38) of the patient 14 in one or more transverse scans 33. Along each scan, data will be collected associated with different rays of the fan beam 24 measuring attenuation at two distinct x-ray energy levels. The two measurements of attenuation for different x-ray energies may be combined to produce a bone image substantially independent of attenuation by soft tissue.

Referring now to FIG. 4, in a first step of a stored program executed by computer 26 of FIG. 1, indicated by block 40, patient information is entered into the computer 26. The information may be entered through the keyboard 31 or through a menu structure and mouse 35 or by transfer of the data from another patient record system.

These data will generally include quantitative information related to risk of fracture other than BMD and will typically include the age and gender of the patient. The present invention also contemplates, however, the use of additional patient information including, for example, the patient's smoking habits (smoker or non-smoker), the amount of exercise the patient performs, the patient's mobility (for example, how much time the patient is on his or her feet during the day or whether the patient can get out of a chair without using his or her arms, or similar measures), the patient's history and patient's family history of fragility fractures, whether there are crush fractures of patient vertebra, and patient hip axis length. These latter two quantities may be determined alternatively by the scanning process described below and input without physician intervention.

After the non-BMD patient information is input at succeeding process block 42, a scan is conducted of the patient to produce a bone image. Typically, as shown in FIG. 1, the scan will be either of a region of interest 38 about the hip of the patient or a region of interest 37 in the area of the lower or lumbar spine region. For the hip, the region of interest 38 may be the femoral neck, trochanter, femoral shaft, Ward's region, or the total femur.

Referring now to FIG. 2, for a bone image 32 of the patient's femur 34, a determination of patient hip axis length 36 may be derived and used as one of the non-BMD inputs described above. Such measurement may be made by the placement of cursors on the image on display 30 by the operator using the cursor control device 35 or through automatic or semi-automatic procedures known in the art in which fiducial points are identified on the bone using a template structure or the like and the distance mathematically calculated.

A similar mechanism may be used to place a measurement region 39 on the neck of the femur 34 defining an area in which the BMD measurements will be combined to yield an average bone density over the measurement region 39.

At process block 44, the average bone density over the measurement region 39 is converted to a standard BMD value according to techniques well known in the art to compensate for differences between densitometers 10 from different manufacturers caused by different definitions of the measurement regions 39 and different measurement techniques.

Next, at process block 46, a T-score is calculated from the standard BMD value. Referring to FIG. 3, such T-scores are well known in the art and compare the average bone density 48 found within the measurement region 39, as corrected by process block 44, to an average bone density 50 of a standard individual. By convention, the standard individual is a statistical combination of individuals of average age thirty and the same gender as the patient. A standard deviation 52 for the standard individual may be determined from measurements of the individuals from whom the standard is prepared. The T-score is then the difference between average bone density 48 (of the patient) and average bone density 50 (of the standard individual) indicated by distance 54 divided by the standard deviation 52.

After computation of the T-score, which may also be output to the operator at process block 56, the present invention computes an absolute fracture risk. The computation of absolute fracture risk may be risk of hip fracture or the risk of any fracture and uses the average bone density 48 (per FIG. 3) and the patient information (per process block 40) of age and gender.

The process of determining absolute fracture risk uses several public data sets. The first data set provides average BMD (or its equivalent) for a normative set of individuals classified by age. Such data is, for example, available from the government sponsored studies, such as the National Health and Nutrition Examination Survey (NHANES) (see www.cdc.gov/nchs/nhanes). This first data set is combined with an empirically determined second data set providing fracture rate for individuals of these same age classifications. The result is an average absolute fracture rate for each age group.

The third data set provides relative risk of fracture for given decreases in BMD for each of the age classifications. This relative risk is made into an absolute risk for the patient by adjusting the average absolute fracture rate for the age group of the patient by the relative risk caused by the difference between the patient's BMD and the average BMD for the patient's age group.

Thus, the absolute fracture risk can be calculated for an individual patient, by determining the deviation of the individual patient's BMD value from the BMD normal to the patient's age group and applying the relative risk for that age group to the absolute fracture risk of that age group to determine the absolute fracture risk for the individual patient.

These relationships may be reduced to a set of curves held in tabular form or to explicit equations according to techniques well known in the art. These data may be smoothed by interpolation to obtain a continuous function. In addition, the absolute fracture estimate can be refined for different countries based on information regarding the relative fracture rates in each country. As additional research is prepared, additional factors may be incorporated into these equations or curves.

The underlying data and this methodology is described generally in the following public papers: "Meta-Analysis Of How Well Measures Of Bone Mineral Density Predict Occurrence Of Osteoporotic Fractures", Marshall et al., Br. Med. J. 312:1254–1259 (1996); "Risk of Hip Fracture Derived From Relative Risks: An Analysis Supplied to the Population of Sweden", Kanis et al., Osteoporosis Int., 11:120–127 (2000); "Prospective: The Diagnosis of Osteoporosis", Kanis et al., J. Bone Miner. Res., Vol. 9, No. 8:1137–1141(1994); "Ten Year Probabilities of Osteoporotic Fractures According to BMD and Diagnostic Thresholds", Kanis et al., J. Bone Miner. Res. Vol. 16 (Suppl 1):S194 (2001), Kanis et al.; "Ten Year Probabilities of Osteoporotic Fractures According to BMD and Diagnostic Thresholds", De Laet et al., J. Bone Miner. Res. Vol. 13, No. 10:1587–1593 (2002); "Identification and Fracture Outcomes of Undiagnosed Low Bone Mineral Density in Post-Menopausal Women: Results From the National Osteoporosis Risk Assessment", Siris et al., JAMA Vol. 286 No. 22:2815–2822 (2001).

These results may be modified by a number of multipliers for risk known in relationships with the other patient input variables. For example, each 6 mm increase in hip axis length (compared to height- and weight-adjusted average) increases risk by a factor of 1.6. A smoker has an increased risk for fracture of 1.3 compared to non-smokers. Subjects with low mobility (less than 4 hours of time on their feet per day) or who are unable to raise from a chair without the use of their arms have an increased fracture risk of 2.0 in each case. In the presence of these or other additional risk factors, absolute risk estimates can be further refined by multiplying the risk determined from the BMD and age models by the appropriate relative risk coefficients reported in the scientific literature.

At succeeding process block 58, the results of the absolute risk calculation may be output. Referring to FIG. 5, in a graphical output, the T-score may form a vertical axis of a graph 59 with patient age as the horizontal axis. The patient's T-score, as computed at process block 46, is plotted on the graph as plot point 60 for the patient's input age.

The background of the graph includes three separate bands 62, 64 and 66 representing low, medium, and high absolute fracture risks, respectively. Generally, band 62 indicates low absolute fracture risk (colored green in this example), band 64, positioned below band 62, indicates medium absolute fracture risk (colored yellow in this example), and band 66, positioned below band 62, and indicates a high absolute fracture risk, (colored red in this example).

The interface between band 62 and 64 indicates a 10% fracture risk during the next ten years and the interface between bands 64 and 66 indicates a 20% fracture risk during the next ten years. This selection of thresholds of 10% and 20% conforms to thresholds used for the treatment of high blood cholesterol in adults as determined by the National Cholesterol Education Project (NCEP) and thus is familiar to physicians. The strength of the relationship between fractures and bone density, however, is stronger than the analogous relationship between lipid levels and coronary heart disease.

The alignment of the three bands 62, 64, and 66 with T-score also provides a classification of the patient that conforms generally to a division prepared by the World Health Organization for the assessment of osteoporosis in populations. Thus, at age 65, when the fracture risk increases significantly, a ten year risk for any fracture of 20% occurs at the femoral T-score of −2.5 matching the WHO category of osteoporosis based on a BMD 2.5 or more standard deviations below a young adult BMD. Likewise, a ten year risk for any fracture of 10% at age 65 equates to a femoral neck T-score of −1 matching the WHO category of low bone mass (osteopenia) based on a BMD between 1 and 2.5 standard deviations below a young adult BMD. Thus, the graphic representation provides consistency with the well known categorizations of normal, osteopenia, and osteoporosis defined by the WHO at an age where fracture risk incidence begins to increase dramatically (65 years). However, it is important to recognize that the WHO criteria were defined for populations rather than individuals.

Note that the bands generally rise with age reflecting the fact that for a given BMD value, risk increases as the patient becomes older. This must be compared to standard BMD and T-score values which remain constant for a given bone mass with the aging process. The particular shape of the bands 62, 64 and 66 will depend on the patient data used. If additional risk factors are included, these bands may be shifted by those risk factors.

Referring to FIG. 6, the information may also be provided in tabular form with a first row of a table 70 providing in a first column, the patient's name and age, in the second column, the ten year risk for hip fracture, and in a third column, the ten year risk for any fracture. In a second row, the first column indicates a reference population having the same age as that of the patient. In a second column of the second row, the ten year risk for hip fracture for that population is provided, and in a third column, the ten year risk for any fracture for that population is provided.

Referring now to FIG. 7, the densitometer 10 of FIG. 1 also may be employed for the measurement of BMD from a region of interest 63 located in a trabecular region of a lumbar vertebra 65. Standard morphometric techniques may be used to detect crushed vertebra 65' such as indicate fragility fractures which may also be used in the calculation of absolute risk as one of the patient input factors described above. Presence of a fragility fracture represents a strong risk factor for future osteoporotic fractures, which can be incorporated into the absolute risk model.

Figure 8:
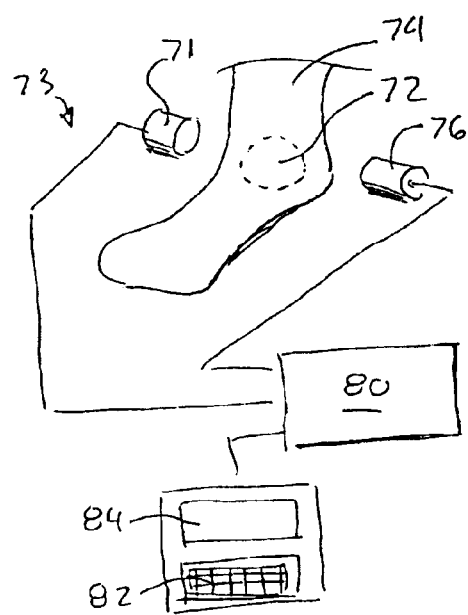
FIG. 8 is a simplified perspective view of an ultrasound bone densitometer measuring the os calcis of the heel.

Referring to FIG. 8, the present invention is also applicable to ultrasonic densitometers 73 in which an ultrasonic transducer 71 provides an ultrasonic signal passing through the os calcis 72 of a patient's foot 74. The ultrasonic signal is received by a detector 76 and processed by computer 80 to determine speed of sound (SOS) or broadband ultrasonic attenuation (BUA) or combinations of the two as are well known in the art. Patient data may be entered through an associated keyboard 82 and output data provided on output display 84 according to well-known techniques in the art.

Thus, the present invention, by accepting additional patient data, provides an accurate measurement of absolute risk, rather than relative risk, as is desired by patients and physicians. Absolute risk assessment is a more accurate representation of risk than T-scores or relative risk measures that can either overstate, in the case of younger individuals, or understate, in the case of the elderly, the true fracture risk.

What is claimed is:

1. A computerized densitometer comprising:
   an energy source and detector opposable about a patient to produce signals indicating energy modification by bone of the patient;
   means for receiving patient information other than energy modification information;
   a computer receiving the signals and patient information and executing a stored program to:
   (a) control the energy source and detector to acquire energy modification signals for a plurality of points over a scan area;
   (b) calculate, for the plurality of points, bone density;
   (c) determine from the bone density and patient information, an absolute risk of bone fracture in the patient over a predetermined period of the future; and
   (d) output the absolute risk of bone fracture, wherein the patient information includes at least one of: habit of smoking; habit of exercise, patient mobility; and patient hip axis length.

2. The computerized densitometer of claim 1 wherein the energy source is a source of ultrasound and the computerized densitometer is an ultrasonic densitometer.

3. The computerized densitometer of claim 1 wherein the scan area is the os calcis.

4. The computerized densitometer of claim 1 wherein the energy source is an x-ray source and the computerized densitometer is an x-ray densitometer.

5. The computerized densitometer of claim 1 wherein the scan area a portion of the femur, selected from a group consisting of the femoral neck, trochanter, femoral shaft, Ward's region, and the total femur.

6. The computerized densitometer of claim 1 wherein the scan area is at least one vertebra.

7. The computerized densitometer of claim 1 wherein the x-ray source provides dual energies of x-rays and the detector operates to distinguish between attenuation at each of the dual energies.

8. The computerized densitometer of claim 1 wherein the output of absolute risk is a risk of hip fracture for the patient.

9. The computerized densitometer of claim 8 wherein the predetermined period of the future is ten years, wherein the output further includes average absolute risk of hip fracture for a period of the future of ten years for a population of the same age and gender as the patient.

10. A computerized densitometer comprising:
an energy source and detector opposable about a patient to produce signals indicating energy modification by bone of the patient;
means for receiving patient information other than energy modification information;
a computer receiving the signals and patient information and executing a stored program to:
(a) control the energy source and detector to acquire energy modification signals for a plurality of points over a scan area;
(b) calculate, for the plurality of points, bone density;
(c) determine from the bone density and patient information, an absolute risk of bone fracture in the patient over a predetermined period of the future; and
(d) output the absolute risk of bone fracture; and
a graphics output device wherein the output of absolute risk is a point plotted on a graph having a vertical axis related to bone mineral density and a horizontal axis of patient age, the graph further having delineated bands defining regions of absolute risk of fracture.

11. The computerized densitometer of claim 10 wherein the delineated bands indicate lines of 10% and 20% absolute risk of fracture.

12. The computerized densitometer of claim 11 wherein the area of the graph in a region of less than 10% absolute risk of fracture is green, the area of the graph in a region between 10% and 20% absolute risk of fracture is yellow and the area of the graph in a region of greater than 20% absolute risk of fracture is red.

13. The computerized densitometer of claim 10 wherein the vertical axis of the graph is T-score.

14. The computerized densitometer of claim 11 wherein the vertical axis of the graph is T-score and wherein the line of 10% absolute risk of any fracture crosses age 56 at a T-score of −1.0 and the line of 20% absolute risk of any fracture crosses age 65 at a T-score of −2.5%.

15. A computerized densitometer comprising:
an energy source and detector opposable about a patient to produce signals indicating energy modification by bone of the patient;
means for receiving patient information other than energy modification information;
a computer receiving the signals and patient information and executing a stored program to:
(a) control the energy source and detector to acquire energy modification signals for a plurality of points over a scan area;
(b) calculate, for the plurality of points, bone density;
(c) determine from the bone density and patient information, an absolute risk of bone fracture in the patient over a predetermined period of the future; and
(d) output the absolute risk of bone fracture for the patient, and wherein the output further includes an average absolute risk of fracture for a period of the future for a population of the same age and gender as the patient.

16. The computerized densitometer of claim 15 wherein the output of absolute risk is a risk of any bone fracture for the patient.

17. The computerized densitometer of claim 16 wherein the predetermined period of the future is ten years.

18. The computerized densitometer of claim 17 wherein the output further includes average absolute risk of any bone fracture for a period of the future of ten years for a population of a same age and gender as the patient.

19. The computerized densitometer of claim 15 wherein the scan region is femur and wherein the computer further executes the stored program to measure a patient hip axis length and wherein the measured patient hip axis length is used as the patient information.

20. A computerized densitometer comprising:
an energy source and detector opposable about a patient to produce signals indicating energy modification by bone of the patient;
a device that receives patient information other than energy modification information, wherein the patient information includes primary information including at least one of information regarding patient age and information regarding patient gender, and further includes secondary information concerning at least one characteristic other than patient age and patient gender;
a computer receiving the signals and patient information and executing a stored program to:
(a) control the energy source and detector to acquire energy modification signals for a plurality of points over a scan area;
(b) calculate, for the plurality of points, bone density;
(c) determine from the bone density and the primary information, an absolute risk of bone fracture in the patient; and
(d) further determine in an additional operation a modified absolute risk of bone fracture from the absolute risk of bone fracture and the secondary information.

21. The computerized densitometer of claim 20, wherein the secondary information concerns at least one of habit of smoking; habit of exercise, patient mobility; patient history of fragility fractures, and patient hip axis length, and wherein the modified absolute risk is determined by multiplying the absolute risk by at least one multiplier corresponding to the secondary information.

* * * * *